United States Patent [19]
Shields

[11] Patent Number: 4,982,745
[45] Date of Patent: Jan. 8, 1991

[54] SELF-ELEVATING LIMB SUPPORT

[76] Inventor: Jack C. Shields, 51916 Continental Ct., Granger, Ind. 46580

[21] Appl. No.: 506,585

[22] Filed: Apr. 9, 1990

Related U.S. Application Data

[63] Continuation of Ser. No. 297,052, Jan. 17, 1989, abandoned.

[51] Int. Cl.⁵ .............................................. A61F 5/37
[52] U.S. Cl. ...................................... 128/877; 5/443; 128/DIG. 15; 128/80 R
[58] Field of Search ............... 128/869, 877, 878, 879, 128/881, 882, 87 R, 89 R, 118; 5/443; 248/118

[56] References Cited
U.S. PATENT DOCUMENTS

| | | | |
|---|---|---|---|
| 2,663,295 | 12/1953 | Lewandowski et al. | 128/881 |
| 2,679,842 | 6/1954 | Brill | 128/878 |
| 3,345,656 | 10/1967 | Steinman | 5/443 |
| 3,903,878 | 9/1975 | Spann | 128/77 |
| 4,104,746 | 8/1978 | Goetz | 5/443 |

Primary Examiner—Robert A. Hafer
Assistant Examiner—Lynda M. Cofsky
Attorney, Agent, or Firm—Todd A. Dawson

[57] ABSTRACT

A limb support for elevating the distal end of a patient's limb. The support is formed from a generally conical body having a longitudinal through bore for accommodating the patient's limb. The distal end of the limb is positioned adjacent the base of the conical body to elevate the end when the limb support rests on a supporting structure. A portion of the conical body may be open to permit bending of the patient's elbow or knee joint.

4 Claims, 2 Drawing Sheets

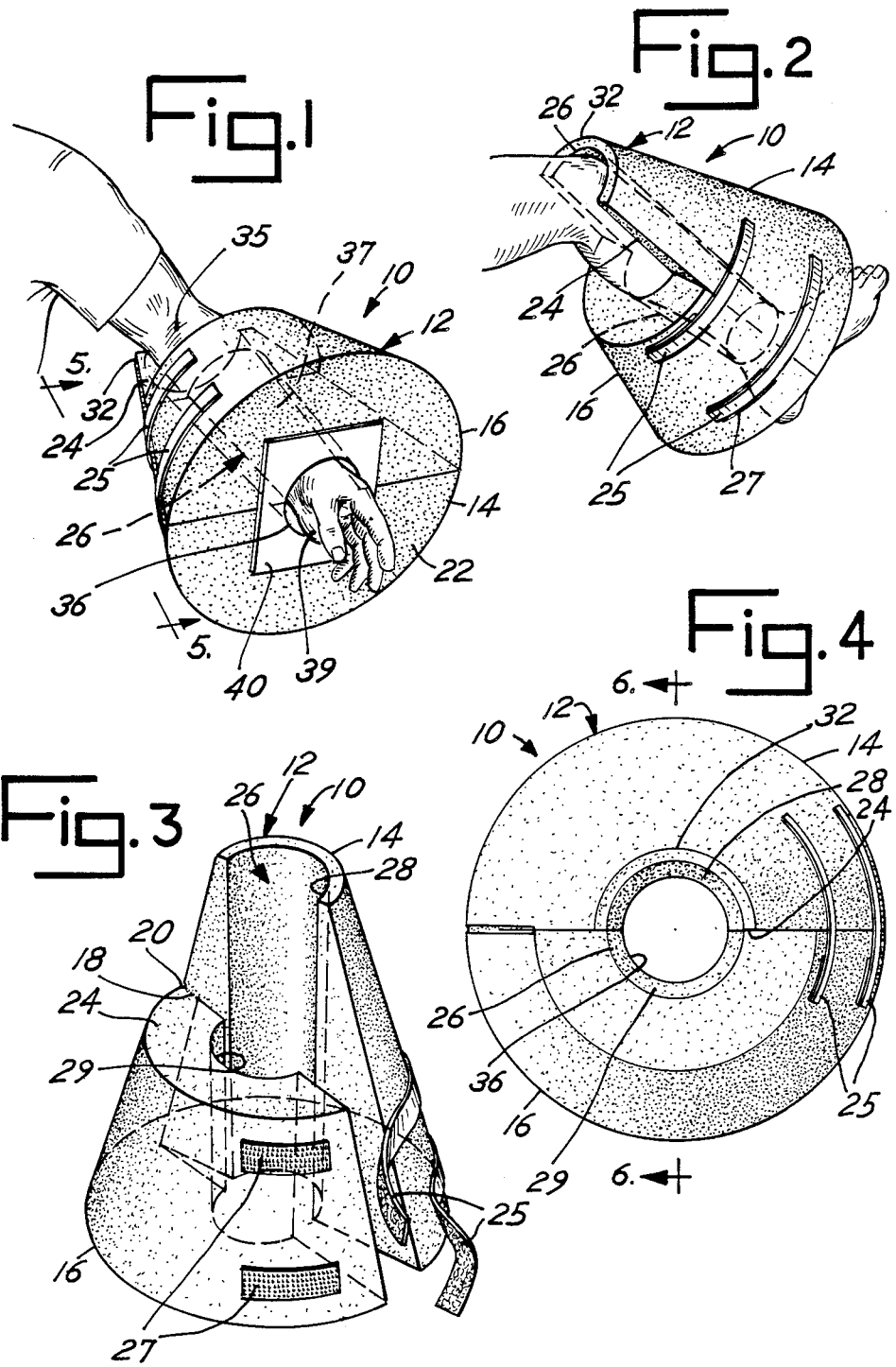

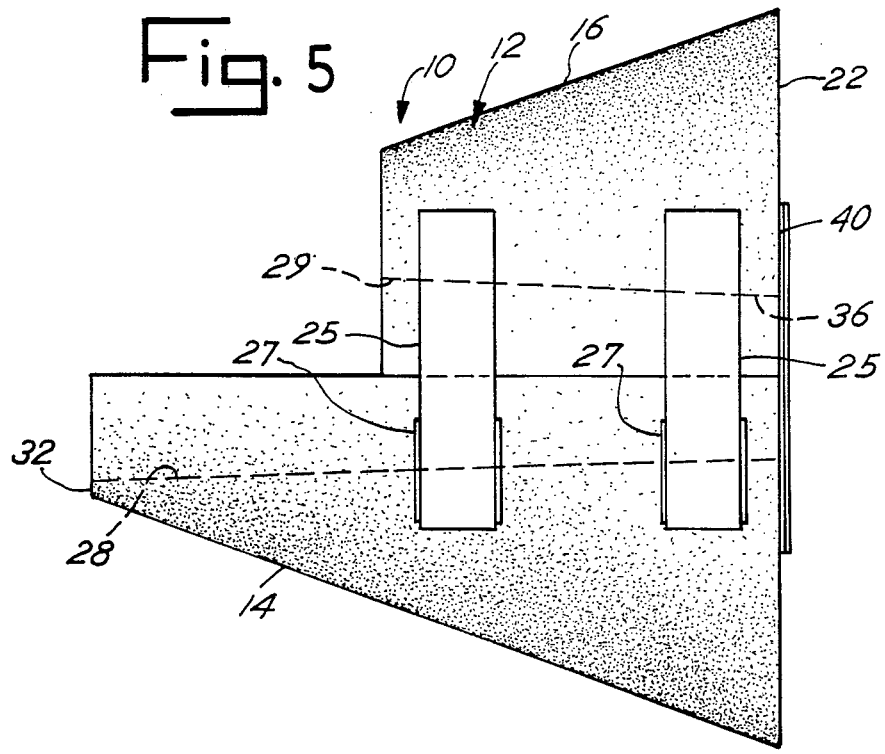
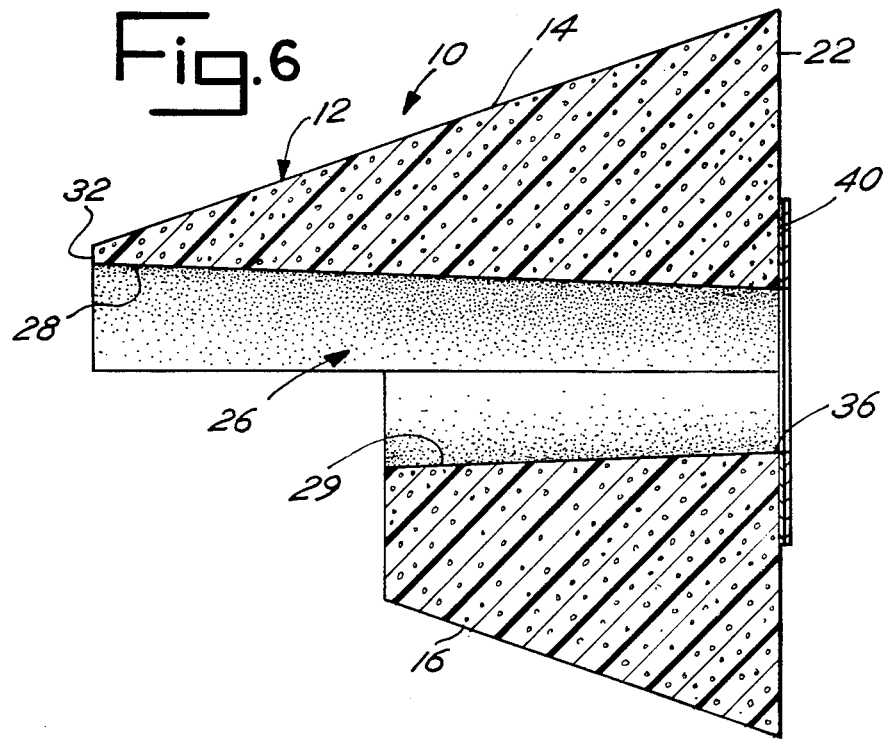

SELF-ELEVATING LIMB SUPPORT

This is a continuation of co-pending application Ser. No. 297,052 filed on Jan. 17, 1989 now abandoned.

SUMMARY OF THE INVENTION

This invention relates to a limb support and will have specific reference to a self-elevating limb support.

Heretofore, to elevate the distal end of a patient's limb relative to the torso for therapeutic purposes, a support stack of pillows was often suggested. While this system is adequate while the patient is awake, there are obvious problems during slumber. The main problem is that if the patient moves his limb during slumber there ia a great chance that the limb may be moved off the support and into a non-elevated condition. A second type of limb elevational device requires an overhead pulley and rope configuration with the limb distal end supported by the rope in mid air. An obvious problem with this second type of elevational device is that the patient is restrained from shifting or rolling in the bed due to his appendages overhead suspension.

The limb support of this invention eliminates the problems associated with the prior elevation devices by providing a generally conical shaped wraparound limb support. The support is placed around the patient's limb with the wide base of the support being positioned adjacent the patient's wrist or ankle. In this manner, the distal end of the patient's limb may be supported in a slightly elevated fashion. Since the support conically extends around the patient's limb and is not connected to an overhead structure the patient may freely move his limb during slumber and still maintain the distal end elevated relative to the torso. The support of this invention has an open proximate portion to allow the patient to freely bend his elbow or knee.

Accordingly, it is an object of this invention to provide for a novel limb elevating device.

Another object of this invention is to provide for a self-elevating limb support.

Another object of this invention is to provide for a self-elevating limb support which may be worn on either the lower arm or lower leg of a patient.

Still another object of this invention is to provide for a self-elevating limb support which allows a patient unrestricted movement during slumber.

Still other objects of this invention will become apparent upon a reading of the following description taken with the accompanying drawings.

BRIEF DESCRIPTION OF THE DRAWINGS

FIG. 1 is a perspective view of the limb support attached to a patient's lower arm portion.

FIG. 2 is a perspective view of the limb support attached to a patient's lower leg portion.

FIG. 3 is a perspective view of the limb support in a slightly open position.

FIG. 4 is a top plan view of the limb support.

FIG. 5 is an elevational view as seen from line 5—5 of FIG. 1 but without the arm inserted.

FIG. 6 is a longitudinal-sectional view taken along line 6—6 of FIG. 4.

DESCRIPTION OF THE PREFERRED EMBODIMENT

The preferred embodiment herein disclosed is not intended to be exhaustive or to limit the invention to the precise form disclosed. Rather, it is chosen and described to enable others skilled in the art to utilize its teachings.

As illustrated in the figures, self-elevating support 10 includes a generally frusto-conical body 12 which is preferably formed from a rigid foam material which is light weight. Body 12 is longitudinally divided into integral halves 14, 16. Halves 14, 16 are preferably connected by an integral or "living" hinge 18. A relief channel 20 is formed in body 22 externally along hinge 18 to allow halves 14, 16 to more easily open about the hinge. Body half 16 terminates a partial distance from distal end 22 of body 12 and forms a shoulder 24. A central longitudinal through bore 26 is defined by side walls 28, 29 which converge from proximal end 32 of body 12 towards body bottom end 22. A pair of common loop type straps 25 and hook connectors 27 are attached to halves 14, 16 opposite hinge 18 to fasten the two halves together.

In use with a patients arm, support 10 is positioned about the wrist and forearm 37 with the patient's hand 39 extending through opening 36 in the manner illustrated in FIG. 1. Straps 25 are tightened in typical fashion to retain the patient's limb in bore 26 between body halves 14, 16. Support 10 is positioned such that shoulder 24 of shortened half 16 is adjacent the inside arm fold 35 opposite the patient's elbow. The proper positioning of support 10 in use with the distal portion of a patient's arm is illustrated in FIG. 1. The proper positioning of support 10 on the distal portion of a patient's leg is illustrated in FIG. 2.

The preferred embodiment of this invention includes a pad 40 affixed to distal end 22 of body 12 about opening 36. Pad 40 is formed from the loop part of a common hook and loop type fastener and is provided for attachment of therapeutic aids and other objects to the pad. A strap could extend between support 10 and the patient, such as at the patient's wrist, to prevent the supported limb from falling from the bed. This retainer could be used for stroke patients.

It should be understood that the invention is not to be limited by the precise details above but may be modified within the scope of the appended claims. The example, the body of the support of this invention may be of one piece inflatable material.

I claim:

1. A support for elevating a distal end of a patient's limb relative to a proximal end of the limb, said support comprising a conical-like body having opposite distal and proximal ends, said body distal end having a diameter greater than the diameter at said body proximal end, said body including a central through bore extending from said distal end to said proximal end for accommodating said limb with said body distal end positioned adjacent the distal end of said limb and means for securing said body about said limb.

2. The support of claim 1 and a portion of said body proximal end being recessed with a remaining non-recessed portion of said body proximal end defining a shoulder to be positioned adjacent the outer bend of a patient's joint in said limb.

3. The support of claim 1 wherein said bore is defined by interior side walls, said interior side walls converge from said body proximal end toward said body distal end.

4. The support of claim 1 and a portion of said body proximal end being recessed with a remaining non-recessed portion of said body proximal end defining a shoulder to be positioned adjacent the outer bend of a patient's joint in said limb, said body being longitudinally divided into first and second body portions, said first body portion having said recessed proximal end portion, said first and second body portions constituting means enabling said body to be separated for insertion of said limb therebetween and to then be closed thereabout.

* * * * *